United States Patent
Dominguez et al.

(10) Patent No.: US 10,105,363 B2
(45) Date of Patent: *Oct. 23, 2018

(54) HISTONE DEACETYLASE INHIBITORS AND COMPOSITIONS AND METHODS OF USE THEREOF

(71) Applicant: CHDI Foundation, Inc., New York, NY (US)

(72) Inventors: Celia Dominguez, Los Angeles, CA (US); Vahri Beaumont, New York, NY (US); Ignacio Muñoz-Sanjuán, Los Angeles, CA (US); Roland W. Bürli, Hertfordshire (GB); Alan F. Haughan, Cambridge (GB); Christopher A. Luckhurst, Cambridge (GB); Michael Wall, Saffron Walden (GB); Gilles Raphy, Saffron Walden (GB); Beth Thomas, Saffron Walden (GB)

(73) Assignee: CHDI foundation, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/411,535

(22) Filed: Jan. 20, 2017

(65) Prior Publication Data

US 2017/0224684 A1    Aug. 10, 2017

Related U.S. Application Data

(63) Continuation of application No. 14/776,039, filed as application No. PCT/US2014/022535 on Mar. 10, 2014, now Pat. No. 9,562,021.

(60) Provisional application No. 61/785,759, filed on Mar. 14, 2013.

(51) Int. Cl.
    *A61K 31/505*  (2006.01)
    *C07D 239/26*  (2006.01)

(52) U.S. Cl.
    CPC .......... *A61K 31/505* (2013.01); *C07D 239/26* (2013.01)

(58) Field of Classification Search
    CPC ............................. C07D 239/26; A61K 31/505
    USPC ......................................... 544/335; 514/256
    See application file for complete search history.

(56) References Cited

U.S. PATENT DOCUMENTS

| | | | |
|---|---|---|---|
| 9,562,021 B2 * | 2/2017 | Dominguez | A61K 31/505 |
| 2009/0181943 A1 | 7/2009 | Tessier et al. | |
| 2014/0163009 A1 | 6/2014 | Luckhurst et al. | |
| 2015/0203468 A1 | 7/2015 | Dominguez et al. | |
| 2016/0031863 A1 | 2/2016 | Dominguez et al. | |
| 2016/0031876 A1 | 2/2016 | Dominguez et al. | |
| 2016/0039745 A1 | 2/2016 | Dominguez et al. | |

FOREIGN PATENT DOCUMENTS

| WO | WO 2012/103008 | 8/2012 |
|---|---|---|
| WO | WO 2015/187542 | 2/2015 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer, 84(10): 1424-1431,2001.*
Gura et al., Systems for identifying new drugs are often faulty, Science, 278:1041-1042, 1997.*
Simone, Oncology: Introduction, Cecil Textbook of Medicine, 20th Edition, vol. 1, pp. 1004-1010, 1996.*
Bosseray et al., PubMed Abstract (Pathol Biol (Paris) 50(8): 483-92), 2002.*
Razonable et al., PubMed Abstract (Herpes 10(3): 60-5), 2003.*
Goff, PubMed Abstract (J Gene Med 3(6): 517-28), 2001.*
Damasio, Alzheimer's Disease and related dementias, Cecil Textbook of Medicine, 20th Edition, vol. 2, pp. 1992-1996, 1996.*
Takai et al., "Human Ovarian Carcinoma Cells: Histone Deacetylase Inhibitors Exhibit Antiproliferative Activity and Potently Induce Apoptosis", American Cancer Society, 2004, 101(12), 2760-2770.*
Glaser, "HDAC Inhibitors: Clinical Update and Mechanism-Based Potential," Biochemical Pharmacology, 2007 74(5), 659-671.*
Layzer, Degenerative diseases of the nervous system, Cecil Textbook of Medicine, 20th Edition, vol. 2, pp. 2050-2057, 1996.*
Bosseray et al., PubMed Abstract (Pathol Biol (Paris) 50(8): 483-92), (2002).
C. Colussi et al., "Histone Deacetylase Inhibitors: Keeping Momentum for Neuromuscular and Cardiovascular Diseases Treatment," Pharmacological Research 62 (2010), pp. 3-10.

(Continued)

*Primary Examiner* — Deepak R Rao
(74) *Attorney, Agent, or Firm* — Shepard Mullin Richter & Hampton LLP

(57) ABSTRACT

Provided are certain histone deacetylase (HDAC) inhibitors of Formula I, compositions thereof, and methods of their use.

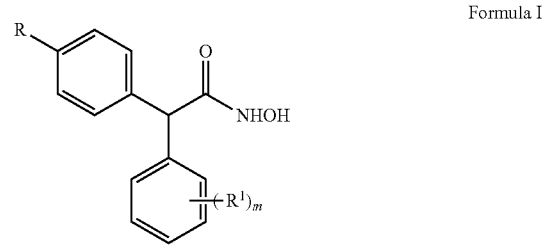

Formula I

14 Claims, 1 Drawing Sheet

(56) References Cited

OTHER PUBLICATIONS

Damasio, Alzheimer's Disease and related dementias, Cecil Textbook of Medicine, 20th Edition, vol. 2, pp. 1992-1996, (1996).
Extended European Search Report for EP 14773968.4 dated Jul. 6, 2016 (6 pages).
Glaser, "HDAC inhibitors: Clinical update and mechanism-based potential, " Biochemical Pharmacology, (2007) 74(5), 659-671.
Goff, PubMed Abstract (1 Gene Med 3(6): 517-28), 2001.
Gura et al., Systems for identifying new drugs are often faulty, Science, 278: 1041-1042, (1997).
International Preliminary Report on Patentability dated Sep. 15, 2015 and International Search Report dated Jul. 8, 2014 for PCT/US2014/022535 (8 pages).
Johnson et al., "Relationships between drug activity in NCI preclinical in vitro and in vivo models and early clincial trials," British Journal of Cancer, 84(10): 1424-1431, (2001).
Layzer, Degenerative diseases of the nervous system, Cecil Textbook of Medicine, 20th Ediition, vol. 2, pp. 2050-2057, (1996).
Pearce et al., "Failure modes in anticancer drug discovery and development," Cancer Drug Design and Discovery Edited by Stephen Neidle, Chapter 18, pp. 424-435 (2008).
Razonable et al., PubMed Abstracct (Herpes 10(3): 60-5), (2003).
Simone, Oncology: Introduction, Cecil Textbook of Medicine, 20th Edition, vol. 1, pp. 1004-1010, (1996).
Takai et al., "Human ovarian carcinoma cells: histone deacetylase inhibitors exhibit antiproliferative activity and potently induce apoptosis", American Cancer Society, (2004), 101(12), 2760-2770.
Bai, et al. Inhibition of class II histone deacetylases in the spinal cord attenuates inflammatory hyperalgesia. Mol Pain. Sep. 7, 2010;6:51. doi: 10.1186/1744-8069-6-51.
Bruneteau, et al. Muscle histone deacetylase 4 upregulation in amyotrophic lateral sclerosis: potential role in reinnervation ability and disease progression. Brain. Aug. 2013;136(Pt 8):2359-68. doi: 10.1093/brain/awt164. Epub Jul. 3, 2013.
Choi, et al. A direct HDAC4-MAP kinase crosstalk activates muscle atrophy program. Mol Cell. Jul. 13, 2012;47(1):122-32. doi: 10.1016/j.molcel.2012.04.025. Epub May 31, 2012.
Kee, et al. Roles and targets of class I and IIa histone deacetylases in cardiac hypertrophy. J Biomed Biotechnol. 2011;2011:928326. doi: 10.1155/2011/928326. Epub Nov. 29, 2010.
Sharma, et al. Targeting histone deacetylases: a novel approach in Parkinson's disease. Parkinsons Dis. 2015;2015:303294. doi: 10.1155/2015/303294. Epub Jan. 28, 2015.
Takahashi-Fujigasaki, et al. Histone deacetylase (HDAC) 4 involvement in both Lewy and Marinesco bodies. Neuropathol Appl Neurobiol. Oct. 2006;32(5):562-6.
Tang, et al. Histone deacetylases as targets for treatment of multiple diseases. Clin Sci (Lond). Jun. 2013;124(11):651-62. doi: 10.1042/CS20120504.
West, et al. New and emerging HDAC inhibitors for cancer treatment. J Clin Invest. Jan. 2014;124(1):30-9. doi: 10.1172/JCI69738. Epub Jan. 2, 2014.

\* cited by examiner

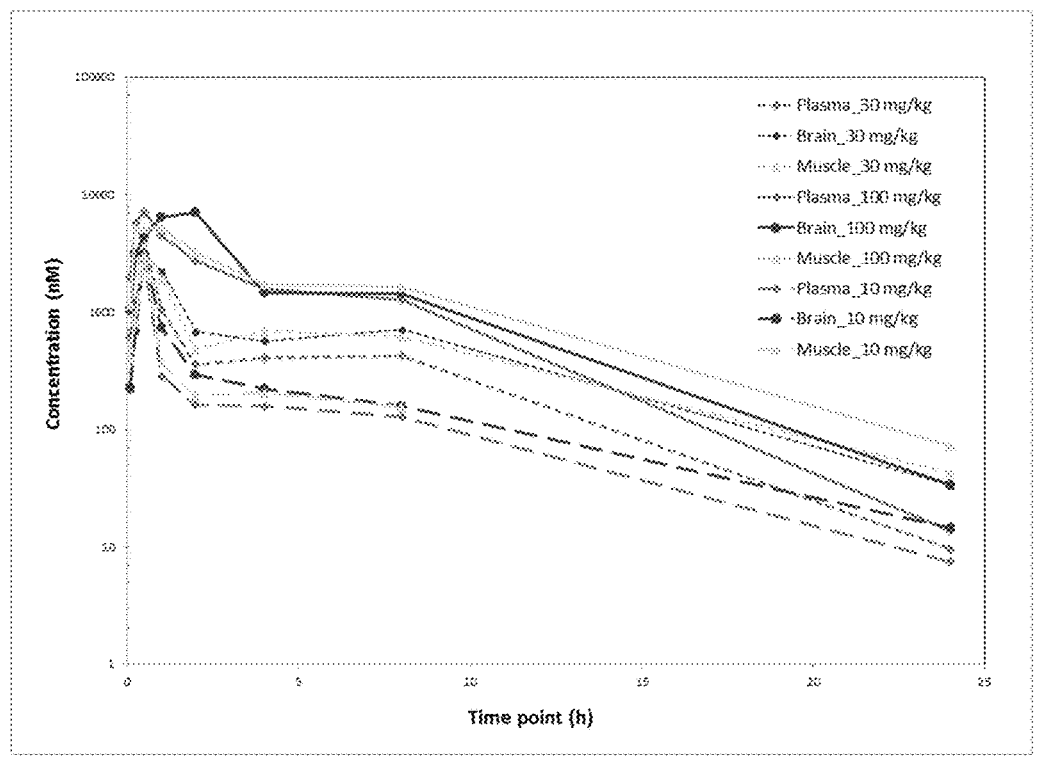

HISTONE DEACETYLASE INHIBITORS AND COMPOSITIONS AND METHODS OF USE THEREOF

This application is a continuation of U.S. application Ser. No. 14/776,039, filed Sep. 14, 2015, which claims the benefit of priority under 35 U.S.C. § 371 of PCT International Application No. PCT/US2014/022535, filed Mar. 10, 2014, which in turn claims the benefit of priority to U.S. provisional application 61/785,759, filed Mar. 14, 2013, which is incorporated herein by reference in its entirety.

Provided herein are certain histone deacetylase (HDAC) inhibitory compounds, compositions thereof, and methods of their use.

Histone deacetylases (HDACs) are zinc-containing enzymes which catalyse the removal of acetyl groups from the ε-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC10 contain two catalytic sites and are classified as Class IIb, whereas HDAC11 has conserved residues in its catalytic center that are shared by both Class I and Class II deacetylases and is sometimes placed in Class IV.

Provided is a compound of Formula I

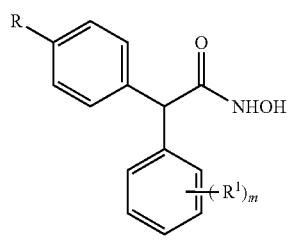

Formula I or a pharmaceutically acceptable salt thereof, wherein
R is pyrimidine substituted with 1 or 2 groups independently chosen from halo, $C_1$-$C_4$ alkyl, and $C_1$-$C_4$ haloalkyl;
each $R^1$ is independently chosen from halo, $C_1$-$C_4$ alkyl, and $C_1$-$C_4$ haloalkyl; and
m is 1, 2 or 3.

Also provided is a pharmaceutical composition comprising a compound, or a pharmaceutically acceptable salt thereof, described herein and at least one pharmaceutically acceptable excipient. Also provided is a method of preparing a pharmaceutical composition comprising a compound, or a pharmaceutically acceptable salt thereof, described herein and at least one pharmaceutically acceptable excipient.

Also provided is a method of treating a condition or disorder mediated by at least one histone deacetylase in a subject in need of such a treatment which method comprises administering to the subject a therapeutically effective amount of a compound, or a pharmaceutically acceptable salt thereof, described herein.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

"$C_1$-$C_4$ Alkyl" encompasses straight chain and branched chain having 1 to 4 carbon atoms. Examples of $C_1$-$C_4$ alkyl groups include methyl, ethyl, propyl, isopropyl, n-butyl, sec-butyl, tert-butyl.

The term "halo" includes fluoro, chloro, bromo, and iodo, and the term "halogen" includes fluorine, chlorine, bromine, and iodine.

The term "$C_1$-$C_4$ haloalkyl" refers to a $C_1$-$C_4$ alkyl wherein 1 to 5 hydrogen atoms are substituted with halo. Non-limiting examples of $C_1$-$C_4$ haloalkyl groups include —CF$_3$, —CHF$_2$, —CFH$_2$, and —CH$_2$CF$_3$.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to anyone of a family of enzymes that remove $N^\epsilon$-acetyl groups from the ε-amino groups of lysine residues of a protein (for example, a histone, or tubulin). Unless otherwise indicated by context, the term "histone" is meant to refer to any histone protein, including H1, H2A, H2B, H3, H4, and H5, from any species. In some embodiments, the histone deacetylase is a human HDAC, including, but not limited to, HDAC-4, HDAC-5, HDAC-6, HDAC-7, HDAC-9, and HDAC-10. In some embodiments, the at least one histone deacetylase is selected from HDAC-4, HDAC-5, HDAC-7, and HDAC-9. In some embodiments, the histone deacetylase is a class IIa HDAC. In some embodiments, the histone deacetylase is HDAC-4. In some embodiments, the histone deacetylase is HDAC-5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, e.g., trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Subject" or "patient' refers to an animal, such as a mammal, that has been or will be the object of treatment, observation or experiment. The methods described herein may be useful in both human therapy and veterinary applications. In some embodiments, the subject is a mammal; and in some embodiments the subject is human.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I, are specifically embraced by herein just as if each and every combination was individually and explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, such as those conditions or disorders mediated by HDAC, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

BRIEF DESCRIPTION OF THE DRAWINGS

Plasma, brain and muscle concentrations of Compound 8 following PO administration at 10 mg/kg, 30 mg/kg and 100 mg/kg are shown in FIG. 1.

Provided is a compound of Formula I

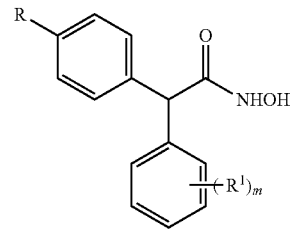

Formula I or a pharmaceutically acceptable salt thereof, wherein
R is pyrimidine substituted with 1 or 2 groups independently chosen from halo, $C_1$-$C_4$ alkyl, and $C_1$-$C_4$ haloalkyl;

each R¹ is independently chosen from halo, $C_1$-$C_4$ alkyl, and $C_1$-$C_4$ haloalkyl; and m is 1, 2 or 3.

In some embodiments, R is

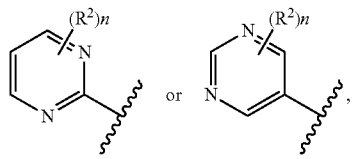

wherein
each R² is independently chosen from halo, $C_1$-$C_4$ alkyl, and $C_1$-$C_4$ haloalkyl;
n is 1 or 2; and
∽ represents the point of connection to the rest of the molecule.

In some embodiments, R is

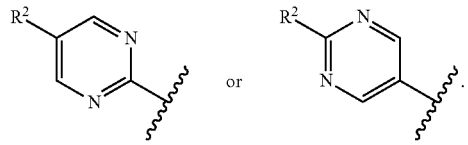

In some embodiments, each R² is independently $C_1$-$C_4$ alkyl. In some embodiments, each R² is $C_1$-$C_4$ haloalkyl.

In some embodiments, each R² is independently methyl or trifluoromethyl.

In some embodiments, n is 1.

In some embodiments, n is 1, and R² is methyl. In some embodiments, n is 1, and R² is trifluoromethyl.

In some embodiments, R is

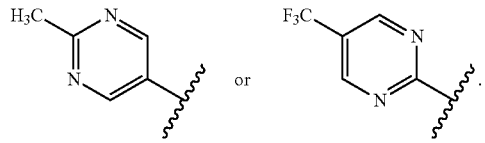

In some embodiments, m is 1.

In some embodiments, at least one R¹ is halo.

In some embodiments, at least one R¹ is fluoro.

In some embodiments, m is 1, and R¹ is 2-fluoro.

Also provided is a compound which is chosen from 2-(2-fluorophenyl)-N-hydroxy-2-(4-(2-methylpyrimidin-5-yl)phenyl)acetamide and 2-(2-fluorophenyl)-N-hydroxy-2-(4-(5-(trifluoromethyl)pyrimidin-2-yl)phenyl)acetamide, or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. Also provided is a use of at least one compound, or pharmaceutically acceptable salt thereof, described herein in the manufacture of medicament for inhibiting at least one histone deacetylase. Also provided is at least one compound, or pharmaceutically acceptable salt thereof, described herein for use in a method for inhibiting at least one histone deacetylase. In some embodiments, the at least one histone deacetylase is a Class IIa HDAC. In some embodiments, the at least one histone deacetylase has homology to yeast HDA1. In some embodiments, the at least one histone deacetylase is selected from HDAC-4, HDAC-5, HDAC-7, and HDAC-9. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC-4 and/or HDAC-5.

Also provided is a method of treating a condition or disorder mediated by HDAC in a subject in need of such a treatment, comprising administering to the subject a therapeutically effective amount of at least one compound, or pharmaceutically acceptable salt thereof, described herein. Also provided is a use of at least one compound, or pharmaceutically acceptable salt thereof, described herein in the manufacture of medicament for the treatment of a condition or disorder mediated by HDAC. Also provided is at least one compound, or pharmaceutically acceptable salt thereof, described herein for use in a method for the treatment of the human or animal body by therapy. Also provided is at least one compound, or pharmaceutically acceptable salt thereof, described herein for use in a method for the treatment of a condition or disorder.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), dentatorubral pallidolusyian atrophy (DRPLA), Friedreich's ataxia, Rubenstein-Taubi syndrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, retinitis pigmentosa, Leber's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficiency, choroidal thrombosis, carotid artery ischemia, contusive ocular injury, retinopathy of permaturity, retinal vein occlusion, proliferative vitreoretinopathy, corneal angiogenesis, retinal microvasculopathy, and retinal edema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture. Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; and the sensitization of tumors to radiotherapy by administering the compound according to the invention before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, iritis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NOMID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cirrhosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrocyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein. Accordingly, also provided is a method of treating a viral disorder, wherein blood cells become sensitized to other treatments after HDAC inhibition, that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is an immune disorder that may be co-treated with TNFα or other immune modulators, upon administering to the subject a therapeutically effective amount of at least one compound, or pharmaceutically acceptable salt thereof, as described herein. Accordingly, also provided is a method of treating an immune disorder that is mediated by HDAC in a subject in need of such a treatment, comprising administering to the subject a therapeutically effective amount of at least one compound, or pharmaceutically acceptable salt thereof, described herein, either before, during, or after a treatment with TNFα or other immune modulators.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein. In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well know to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients. A compound of the present invention can be formulated into pharmaceutical compositions using techniques well known to those in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined.

The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Furthermore, pharmaceutical compositions containing the compound, or pharmaceutically acceptable salt thereof, described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL® RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Desipramine, Nortriptyline, Paroxetine, Fluoxetine, Sertraline, Tetrabenazine, Haloperidol, Chlorpromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Desipramine, Nortriptyline, Paroxetine, Fluoxetine, Sertraline, Tetrabenazine, Haloperidol, Chlorpromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Desipramine, Nortriptyline, Paroxetine, Fluoxetine, Sertraline, Tetrabenazine, Haloperidol, Chlorpromazine, Thioridazine, Sulpride, Quetiapine, Clozapine, and Risperidone.

Also provided are methods for treating Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl®, Cognex®, Aricept®, Exelon®, Akatinol®, Neotropin™, Eldepryl®, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl®, Cognex®, Aricept®, Exelon®, Akatinol®, Neotropin™, Eldepryl®, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to, Reminyl®, Cognex®, Aricept®, Exelon®, Akatinol®, Neotropin™, Eldepryl®, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents:

(i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin $\alpha_v\beta_3$ function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

The present disclosure includes all isotopes of atoms occurring in the compounds and pharmaceutically acceptable salts thereof described herein. Isotopes include those atoms having the same atomic number but different mass numbers. The present disclosure also includes every combination of one or more atoms in the compounds and pharmaceutically acceptable salts thereof described herein that is replaced with an atom having the same atomic number but a different mass number. One such example is the replacement of an atom that is the most naturally abundant isotope, such as $^1H$ or $^{12}C$, found in one of the compounds and pharmaceutically acceptable salts thereof described herein, with a different atom that is not the most naturally abundant isotope, such as $^2H$ or $^3H$ (replacing $^1H$), or $^{11}C$, $^{13}C$, or $^{12}C$ (replacing $^{12}C$). A compound wherein such a replacement has taken place is commonly referred to as being isotopically-labeled. Isotopic-labeling of the compounds and pharmaceutically acceptable salts thereof described herein can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$ an $^{131}I$. Also provided are pharmaceutical compositions comprising a compound or a pharmaceutically acceptable salt thereof described herein, wherein the naturally occurring distribution of the isotopes in the pharmaceutical composition is perturbed. Also provided are pharmaceutical compositions comprising a compound or a pharmaceutically acceptable salt thereof described herein enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC. Certain isotopically-labeled compounds and pharmaceutically acceptable salts thereof described herein are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds and pharmaceutically acceptable salts thereof described herein can generally be prepared by following procedures analogous to those disclosed in the Examples infra, by substituting an isotopically labeled reagent for a non-isotopically labeled reagent. Moreover, it should be understood that all of the atoms represented in the compounds and pharmaceutically acceptable salts thereof described herein can be either the most commonly occurring isotope of such atoms or a scarcer radio-isotope or nonradioactive isotope.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

As used herein, the following abbreviations have the following meanings. If an abbreviation is not defined, it has its generally accepted meaning.

Abbreviations aq.: Aqueous
AUC: Area under curve
[bmim][PF$_6$]: 1-Butyl-3-methylimidazolium hexafluorophosphate
BOP: Benzotriazole-1-yl-oxy-tris-(dimethylamino)-phosphonium hexafluorophosphate
conc.: Concentrated
d: Doublet
DCM: Dichloromethane
DCE: Dichloroethane
DIPEA: Diisopropyle thylamine
DMA: Dimethylacetamide
DME: Dimethoxyethane
DMF: Dimethylformamide
DMSO: Dime thylsulfoxide
eq.: Equivalent
ES+: Electrospray Positive Ionisation
ES−: Electrospray Negative Ionisation
Et$_2$O: Diethyl ether
EtOAc: Ethyl acetate
g: Gram
h: Hour
HPLC: High Performance Liquid Chromatography
Hz: Hertz
IV: Intravenous
J: Coupling constant
kg: Kilogram
LCMS: Liquid Chromatography Mass Spectrometry
LiHMDS: Lithium bis(trimethylsilyl)amide
m: Multiplet
M: Mass
MeCN: Acetonitrile
MeOH: Methanol
mg: Milligram
min: Minute
mL: Milliliter
mmol: Millimole
ng: Nanogram
nM: Nanomolar
NMP: N-Methyl pyrrolidinone
N.M.R.: Nuclear magnetic resonance
Pd/C: Palladium on carbon
Pd$_2$(dba)$_3$: Tris(dibenzylideneacetone)dipalladium(0)
Pd(dppf)Cl$_2$: [1,1'-Bis(diphenylphosphino)ferrocene]dichloropalladium(II)
Pd(PPh$_3$)$_4$: Tetrakis(triphenylphosphine)palladium(0)
PO: Oral
o-tol: ortho-Tolyl
Rf: Retention factor
Rh$_2$(OAc)$_4$: Rhodium(II) acetate
RT or R$_t$: Retention time
r.t.: Room temperature
RuPhos: 2-Dicyclohexylphosphino-2',6'-di-iso-propoxy-1,1'-biphenyl
s: Singlet
THF: Tetrahydrofuran
TMSCN: Trimethylsilyl cyanide
w/v: Weight to volume
Xantphos: 4,5-Bis(diphenylphosphino)-9,9-dimethylxanthene
μL: Microliter
μM: Micromolar Example 1. Synthesis of methyl 2-(4-bromophenyl)-2-(2-fluorophenyl)acetate (4)

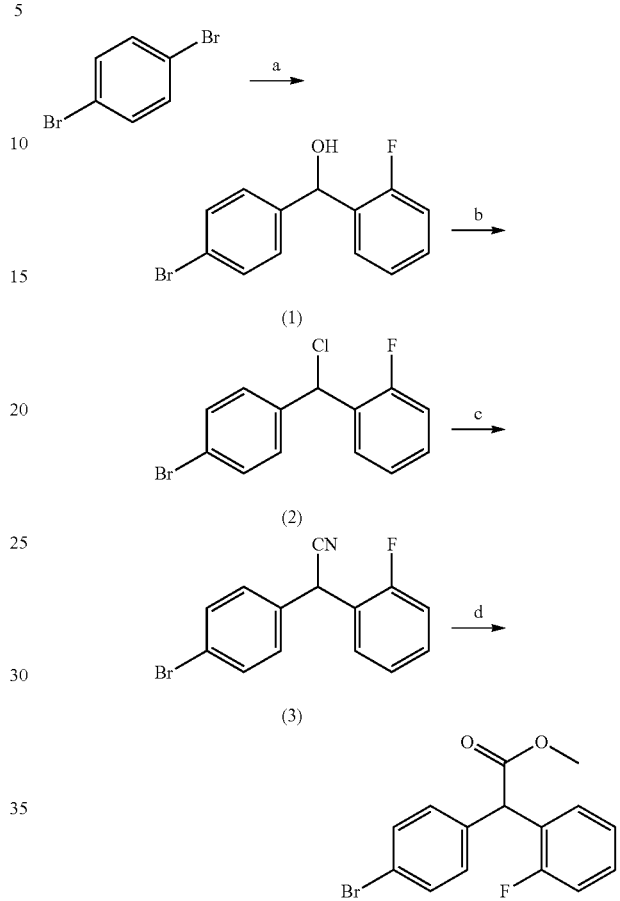

Reagents and conditions: a. Mg, Et$_2$O; 2-fluorobenzaldehyde, (55% yield); b. SOCl$_2$, DCM, r.t., (94% yield); c. TMSCN, TiCl$_4$, DCM, r.t., (99% yield); d. MeOH, conc. H$_2$SO$_4$, reflux, (63% yield).

a. Synthesis of (4-bromophenyl)(2-fluorophenyl)methanol (1)

This reaction was performed under nitrogen. Magnesium (5.2 g, 214 mmol; 1.1 eq.) was covered with ether (40 mL) in a 1 L round bottom flask equipped with a refluxing condenser and a pressure equalizing dropping funnel. A solution of 1,4-dibromobenzene (45.8 g, 194 mmol) in ether (200 mL) was added dropwise at a rate sufficient to first initiate and then sustain reflux over a 1.5 h period. A few crystals of iodine were used to initiate the reaction. After complete addition, the reaction mixture was stirred at r.t. for 1 h. The mixture was cooled to 0° C. (ice bath) and a solution of 2-fluorobenzaldehyde (22.5 mL, 26.6 g, 214 mmol; 1.1 eq.) in ether (45 mL) was added dropwise over 20 min. The mixture was left to warm up to r.t. and was stirred overnight. The reaction mixture was cooled to 0° C. (ice-bath) and quenched with a mixture of aqueous NH$_4$Cl (50 mL) and 2 M HCl (50 mL). EtOAc (100 mL) was added and the mixture was filtered through Celite®, washing with EtOAc (2×50 mL). The two phases were separated and the organic phase was washed with brine (70 mL), dried (MgSO$_4$), filtered and concentrated in vacuo to give a yellow oil (59 g). Purification by flash column chromatography using 10% EtOAc in isohexane (400 g of silica; column diameter: 80 mm) (R$_f$ 0.26) gave the subtitle compound as a yellow oil (29.83 g, 55% yield). LCMS(R$_t$ 3.17 min, [M−OH]+ 263/265).

b. Synthesis of 1-((4-bromophenyl)chloromethyl)-2-fluorobenzene (2)

The reaction was carried out under nitrogen. To a solution of compound 1 (29.76 g, 105.85 mmol) in DCM (150 mL) cooled to 0° C. (ice-bath) was added thionyl chloride (8.5 mL, 13.85 g, 116.44 mmol, 1.1 eq.). The reaction mixture was left to warm up to r.t. and was stirred for 72 h. The mixture was poured into 2M Na$_2$CO$_3$ (150 mL). The two phases were separated and the organic layer was washed with brine (2×50 mL), dried (MgSO$_4$), filtered and concentrated in vacuo to give the subtitle compound as a yellow oil (29.8 g, 94% yield). LCMS(R$_t$ 3.67 min, [M+H]+ 299 not seen). $^1$H N.M.R. (CDCl$_3$) 7.57-7.40 (m, 3H), 7.38-7.28 (m, 3H), 7.19-7.15 (m, 1H), 7.07-7.02 (m, 1H), 6.37 (s, 1H).

c. Synthesis of 2-(4-bromophenyl)-2-(2-fluorophenyl)acetonitrile (3)

Compound 2 (29.8 g, 99.62 mmol) was dissolved in dichloromethane (190 mL) and the solution was cooled to 0° C. (ice-bath). Trimethylsilyl cyanide (12.5 mL, 9.88 g, 99.62 mmol) was added followed by titanium(IV) chloride (10.9 mL, 18.9 g, 99.62 mmol). The mixture was left to warm up to r.t. and was stirred overnight. The mixture was poured into ice-water (~300 mL) containing Na$_2$CO$_3$ (50 g), then diluted with more DCM (~200 mL) and filtered through Celite. After separation of the two phases the aqueous layer was re-extracted with DCM (200 mL) and the organic phase was dried (MgSO$_4$), filtered and concentrated in vacuo to give the subtitle compound as an orange oil (28.65 g, 99% yield). LCMS(R$_t$ 3.38 min, [M+H]+ 290/292). $^1$H N.M.R. (CDCl$_3$) 7.52-7.49 (m, 2H), 7.48-7.41 (m, 1H), 7.40-7.31 (m, 2H), 7.29-7.25 (m, 1H), 7.25-7.17 (m, 1H), 7.15-7.07 (m, 1H), 5.39 (s, 1H).

d. Synthesis of methyl 2-(4-bromophenyl)-2-(2-fluorophenyl)acetate (4)

A solution of compound 3 (23.5 g, 80.99 mmol) and c.H$_2$SO$_4$ (24.5 mL) in methanol (175 mL) was heated under reflux for 20 h. LCMS showed mainly a mixture of unreacted starting material (R$_t$ 3.38 min, [M+H]+ 290, 51%) and desired product (R$_t$ 3.44 min, [M+H]+ 324 not seen, 36%). c.H$_2$SO$_4$ (8.2 mL) and MeOH (30 mL) were added and the reaction mixture was heated under reflux for 72 h. LCMS indicated still some unreacted stating material (27%). More c.H$_2$SO$_4$ (8.2 mL) and MeOH (30 mL) were added and the mixture was heated under reflux for a further 20 h. LCMS showed mainly the desired product (R$_t$ 3.44 min, [M+H]+ 324 not seen, 84%). The reaction mixture was cooled to 0° C. (ice-bath) and partitioned between H$_2$O (100 mL) and DCM (400 mL). The two phases were separated and the organic layer was dried (MgSO$_4$), filtered and concentrated in vacuo to give a yellow oil (25.81 g). Purification by flash column chromatography using 3% EtOAc in isohexane (400 g of silica; column diameter: 80 mm) (R$_f$ 0.17) gave the title compound as a pale yellow oil (16.4 g, 63% yield). LCMS (R$_t$ 3.44 min, [M+H]+ 324 not seen). $^1$H N.M.R. (CDCl$_3$) 7.48-7.45 (m, 2H), 7.30-7.18 (m, 4H), 7.12-7.03 (m, 2H), 5.24 (s, 1H), 3.75 (s, 3H).

Example 2. Synthesis of 2-(2-fluorophenyl)-N-hydroxy-2-(4-(2-methylpyrimidin-5-yl)phenyl)acetamide (6)

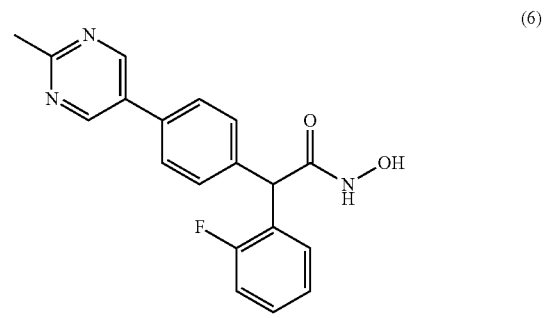 [SMILES: Cc1ncc(-c2ccc(C(C(=O)NO)c3ccccc3F)cc2)cn1]

(6)

Synthesis of methyl 2-(2-fluorophenyl)-2-(4-(2-methylpyrimidin-5-yl)phenyl)acetate (5)

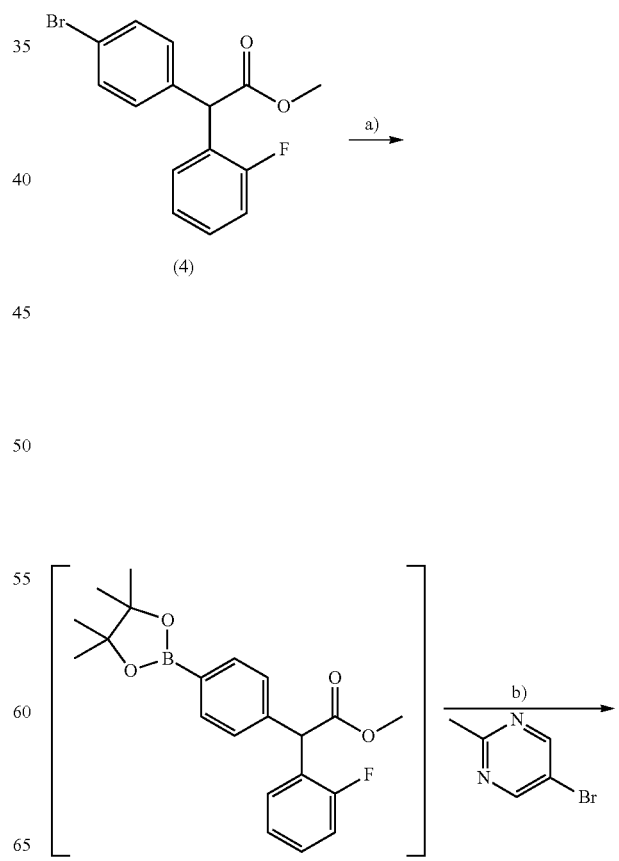

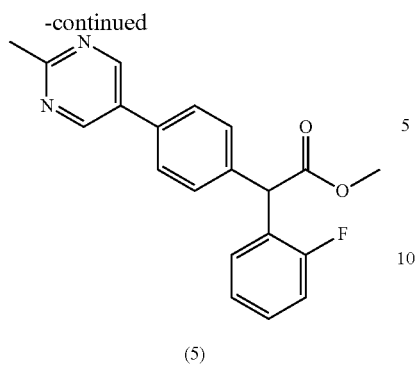

(5)

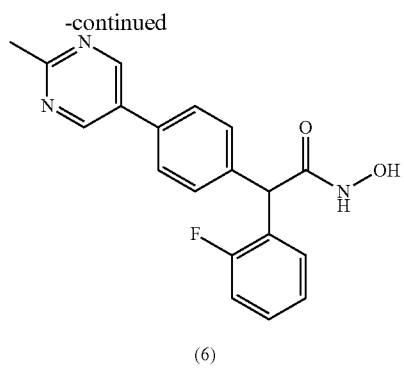

(6)

Reagents and conditions: a) methyl-2-(-4-bromophenyl)-2-(-2-fluorophenyl)acetate, CsF, Pd(PPh₃)₄, DME, MeOH, 100° C., 1 h; b) 2-methyl-2-bromopyrimidine, CsF, Pd(PPh₃)₄, DME, MeOH, 100° C., 1 h (79-85% yield).

Reagents and conditions: 50% aq. hydroxylamine, 15% w/v NaOH, MeOH (70% yield).

Yields (after chromatography) of intermediate ester 5, performed at different scales:

0.3 g of aryl bromide (0.9 mmol) gave 5 in 85% yield;
2.0 g of aryl bromide (6.2 mmol) gave 5 in 79% yield;
4.0 g of aryl bromide (12.4 mmol) gave 5 in 79% yield.

To a solution of methyl-2-(4-bromophenyl)-2-(2-fluorophenyl) acetate (4) (4.0 g, 12.4 mmol) in DME/MeOH (80 mL: 20 mL) was added bis(pinacolato)diboron (3.40 g, 13.4 mmol) and CsF (3.80 g, 25.0 mmol). The mixture was degassed with $N_2$ for 5 min, treated with Pd(PPh₃)₄ (570 mg, 0.5 mmol) and heated at 110° C. for 1 h (LCMS indicated completion of the reaction). 5-Bromo-2-methylpyrimidine (2.50 g, 14.4 mmol), CsF (3.80 g, 25.0 mmol) and Pd(PPh₃)₄ (570 mg, 0.5 mmol) were added to the mixture and heating was continued at 110° C. for 1 h. The mixture was cooled to r.t., treated with water (100 mL) and extracted with DCM (2×100 mL). The combined organic phase was separated, dried (MgSO₄), and concentrated in vacuo. Purification by chromatography (SiO₂) eluting with DCM to remove unreacted boronic esters followed by Et₂O afforded the subtitle compound as a pale yellow oil (3.3 g, 79% yield). LCMS ($R_t$ 2.94 min, [M+H]+ 337) ¹H N.M.R. (CDCl₃) 8.83 (s, 2H), 7.55 (d, 2H, J=6.4 Hz), 7.46 (d, 2H, J=6.4 Hz), 7.32-7.29 (m, 2H), 7.15-7.05 (m, 2H), 5.34 (s, 1H), 3.79 (s, 3H), 2.79 (s, 3H).

Hydroxamic acid formation: 2-(2-fluorophenyl)-N-hydroxy-2-(4-(2-methylpyrimidin-5-yl)phenyl)acetamide To a stirred solution of ester 5 (5.0 g, 15 mmol) in MeOH (40 mL) was added hydroxylamine (10 mL, 50% aqueous solution, 150 mmol) and sodium hydroxide (1.2 g, 30 mmol). The mixture was stirred at r.t. for 2 h, then treated with saturated ammonium chloride solution and extracted into ethyl acetate. The combined organic phase was separated, dried (MgSO₄), and evaporated in vacuo. Purification by trituration with 97:3 DCM/MeOH gave the title compound as a white solid (3.42 g, 70% yield).

LCMS($R_t$ 2.30 min, [M+H]+ 338). 1H N.M.R. (DMSO-d₆) 11.05 (s, 1H), 9.35 (s, 2H), 9.04 (s, 1H), 7.74 (d, 2H, J=8.2 Hz), 7.53 (t, 1H, J=8.2 Hz), 7.42 (d, 2H, J=8.2 Hz), 7.38-7.31 (m, 1H), 7.22-7.17 (m, 2H), 5.08 (s, 1H), 2.66 (s, 3H).

Example 3. Synthesis of 2-(2-fluorophenyl)-N-hydroxy-2-(4-(5-(trifluoromethyl)pyrimidin-2-yl)phenyl)acetamide (8)

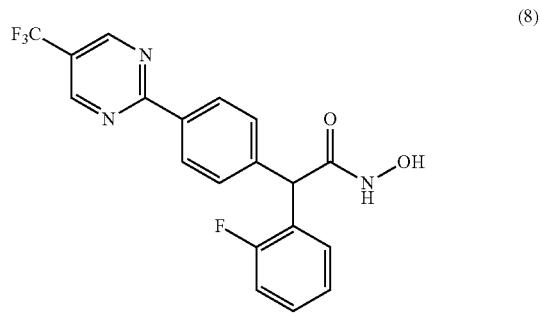 [SMILES: O=C(NO)C(c1ccc(-c2ncc(C(F)(F)F)cn2)cc1)c1ccccc1F]

(8)

Synthesis of methyl 2-(2-fluorophenyl)-2-(4-(5-(trifluoromethyl)pyrimidin-2-yl)phenyl)acetate (7)

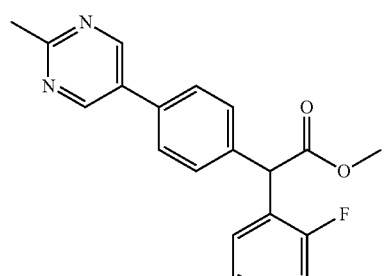

(5)

H₂NOH, MeOH →

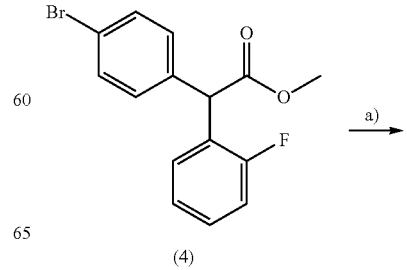

(4)

a) →

-continued

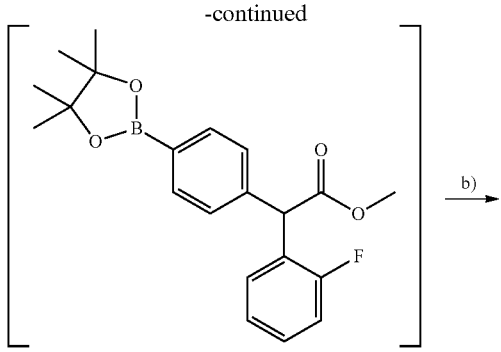

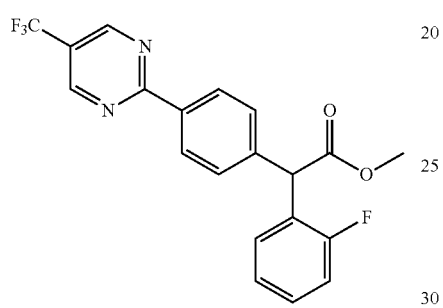

(7)

Reagents and conditions: a) methyl-2-(-4-bromophenyl)-2-(-2-fluorophenyl)acetate, bis(pinacolato)diboron, CsF, Pd(PPh₃)₄, DME, MeOH, 1 h, 100° C. (80% yield); b) 2-chloro-5-trifluoromethylpyrimidine, K₂CO₃, Pd(PPh₃)₄, dioxane, water, 100° C., 16 h (74% yield).

To a stirred solution of methyl-2-(4-bromophenyl)-2-(2-fluorophenyl) acetate (2.0 g, 6.2 mmol) in DME/MeOH (80 mL:20 mL) was added bis(pinacolato)diboron (1.70 g, 7.2 mmol) and CsF (1.90 g, 12.5 mmol). The mixture was degassed with N₂ for 5 min, treated with Pd(PPh₃)₄ (300 mg, 0.3 mmol) and heated at 110° C. for 1 h. The mixture was cooled to r.t., treated with water (100 mL) and extracted with DCM (2×100 mL). The combined organic phase was separated, dried (MgSO₄), and concentrated in vacuo to yield methyl-2-(2-fluorophenyl)-2-(4-(4,4,5,5-tetramethyl-1,3,2-dioxaborolan-2-yl)phenyl)acetate as an orange oil (1.83 g, 80% yield).

To a stirred solution of methyl-2-(2-fluorophenyl)-2-(4-(4,4,5,5-tetramethyl-1,3,2-dioxaborolan-2-yl)phenyl)acetate (1.83 g, 4.8 mmol) in dioxane (80 mL) and water (20 mL) was added 2-chloro-5-trifluoromethylpyrimidine (1.0 g, 5.5 mmol) and K₂CO₃ (1.35 g, 9.8 mmol). The mixture was degassed with N₂ for 5 min, treated with Pd(PPh₃)₄ (280 mg, 0.24 mmol) and heated at 110° C. overnight (LCMS indicated completion of the reaction). The mixture was cooled to r.t., treated with water (100 mL) and extracted with DCM (2×100 mL). The combined organic phase was separated, dried (MgSO₄), and evaporated in vacuo. Purification by chromatography (SiO₂) eluting with isohexane/ethyl acetate (95:5) afforded the subtitle compound as a white solid (1.45 g, 74% yield). LCMS(R$_t$ 3.54 min, [M+H]+ 391). $^1$H N.M.R. (CDCl₃) 9.01 (s, 2H), 8.48 (d, 2H, J=8.4 Hz), 7.47 (d, 2H, J=8.4 Hz), 7.30-7.25 (m, 2H), 7.13-7.05 (m, 2H), 5.38 (s, 1H), 3.78 (s, 3H).

Hydroxamic acid formation: 2-(2-fluorophenyl)-N-hydroxy-2-(4-(5-(trifluoromethyl)pyrimidin-2-yl)phenyl)acetamide (8)

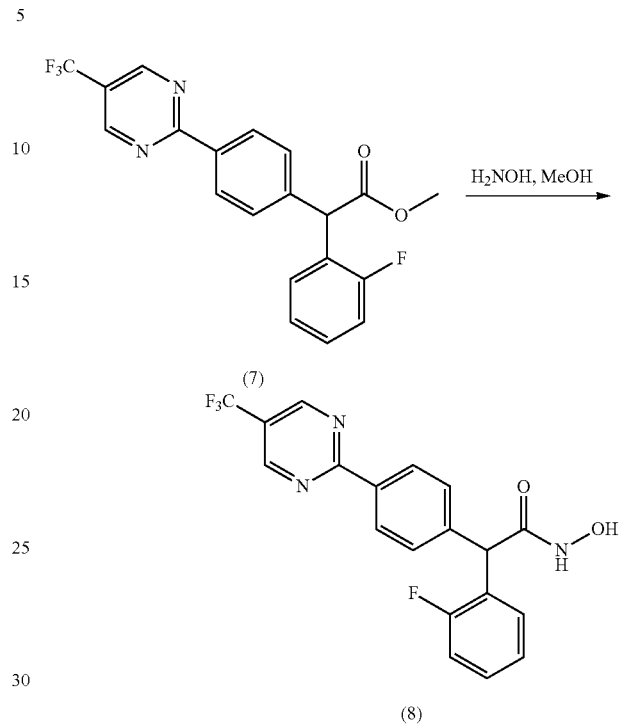

Reagents and conditions: 50% aq. hydroxylamine, 15% w/v NaOH, MeOH (82%yield).

To a stirred solution of methyl-2-(2-fluorophenyl)-2-(4-(5-(trifluoromethyl)pyrimidine-2-yl)phenyl)acetate (6.6 g, 16.9 mmol) in methanol (80 mL) at r.t. was added hydroxylamine (11.0 mL, 50% aqueous solution, 169.0 mmol) and sodium hydroxide (9.0 mL, 15% aqueous solution, 33.8 mmol). The mixture was stirred at r.t. for 2.5 h, treated with water (100 mL) and extracted with DCM (2×50 mL). The aqueous layer was concentrated in vacuo to half bulk, neutralized with saturated NH₄Cl solution (50 mL) and the resulting precipitate was filtered, washed with water and dried. LCMS indicated 80% purity. Recrystallisation from chloroform (40 mL) afforded the title compound as a white solid (5.3 g, 82% yield). LCMS(R$_t$ 2.94 min, [M+H]+ 392). $^1$H N.M.R. (DMSO-d₆) 11.08 (s, 1H), 9.38 (s, 2H), 9.08 (s, 1H), 8.44 (d, 2H, J=8.2 Hz), 7.55-7.49 (m, 3H), 7.37-7.33 (m, 1H), 7.23-7.18 (m, 2H), 5.13 (s, 1H).

Example 4: Analysis of Inhibition of HDAC4

The potency of exemplifying compounds descried herein is quantified by measuring the Histone Deacetylase 4 (HDAC4) catalytic domain enzymatic activity using the Class IIa selective substrate, Boc-Lys(Tfa)-AMC. The substrate is deacetylated to Boc-Lys-AMC by HDAC4. Cleavage by trypsin results in the release of the fluorophore AMC from the deacetylated substrate. The fluorescence of the sample is directly related to the histone deacetylase activity in the sample.

Serially Dilute Compounds.

Serial dilutions of the compounds to be tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% dimethyl sulfoxide (DMSO). Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette (Matrix Technologies Ltd).

TABLE 1

Serial Dilution of Compounds

| Diluted Solutions | Well | Concentration (µM) | Dilution ratio | Volumes |
|---|---|---|---|---|
| Concentration 1 | A | 10000 | — | 60 µL 10 mM Test compound/reference control |
| Concentration 2 | B | 5000 | 1:2 | 30 µL A + 30 µL DMSO |
| Concentration 3 | C | 2500 | 1:2 | 30 µL B + 30 µL DMSO |
| Concentration 4 | D | 1000 | 1:2.5 | 30 µL C + 45 µL DMSO |
| Concentration 5 | E | 500 | 1:2 | 30 µL D + 30 µL DMSO |
| Concentration 6 | F | 250 | 1:2 | 30 µL E + 30 µL DMSO |
| Concentration 7 | G | 125 | 1:2 | 30 µL F + 30 µL DMSO |
| Concentration 8 | H | 62.5 | 1:2 | 30 µL G + 30 µL DMSO |
| Concentration 9 | I | 31.25 | 1:2 | 30 µL 1 H + 30 µL DMSO |
| Concentration 10 | J | 15.63 | 1:2 | 30 µL I + 30 µL DMSO |
| Concentration 11 | K | 7.81 | 1:2 | 30 µL J + 30 µL DMSO |
| Concentration 12 | L | 3.91 | 1:2 | 30 µL K + 30 µL DMSO |
| Concentration 13 | M | 1.95 | 1:2 | 30 µL L + 30 µL DMSO |
| Concentration 14 | N | 0.98 | 1:2 | 30 µL M + 30 µL DMSO |
| Concentration 15 | O | 0.49 | 1:2 | 30 µL N + 30 µL DMSO |
| Concentration 16 | P | 0.24 | 1:2 | 30 µL O + 30 µL DMSO |

2 µL (200×) of each diluted solution and each control (full activity: 100% DMSO alone or full inhibition 1 mM) is stamped into V-bottomed polypropylene 384-well compound plates using either the Bravo (384-well head from Agilent) or 12.5 µL 16-channel Matrix multi-channel pipette (Matrix Technologies Ltd). Each well with the 200× compound solution is diluted 1:20 by the addition of 38 µL assay buffer+DMSO (10.5% DMSO, 45 mM Tris-HCl, 123 mM NaCl, 2.4 mM KCl, and 0.9 mM MgCl$_2$ at pH 8.0 and equilibrated to r.t.).

Prepare HDAC4 Catalytic Domain Enzyme (0.286 µg/mL).

The HDAC4 catalytic domain enzyme is human catalytic domain HDAC4 protein (amino acids 648-1032 (with a C-terminal 6× histidine tag), made and provided by BioFocus at 0.5 mg/mL. A working solution of enzyme is prepared from a 0.5 mg/mL stock aliquot of HDAC4 catalytic domain (thawed on ice) diluted to 0.286 µg/mL with assay buffer (50 mM Tris-HCl, 137 mM NaCl, 2.7 mM KCl, and 1 mM MgCl$_2$ at pH 8 and equilibrated to r.t.) just prior to the addition of the enzyme to the assay.

Prepare 5× (50 µM) Boc-Lys(Tfa)-AMC Substrate.

5× (50 µM) substrate is prepared just prior to the addition to the assay. A 1 mM substrate stock is made by diluting a 100 mM Boc-Lys(Tfa)-AMC in DMSO solution 1:100 by adding it drop-wise to assay buffer (equilibrated to r.t.) while vortexing at slow speed to prevent precipitation. The 5× substrate is prepared by diluting the 1 mM substrate solution 1:20 by adding it drop-wise to assay buffer (equilibrated to r.t.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin (PAA Laboratories Ltd.) equilibrated to r.t.

Assay.

5 µL of each solution of 1:20 diluted compound from above is transferred to a clear bottomed, black, 384-well assay plate using the Bravo or the Janus (384-well MDT head from Perkin Elmer). Using a 16-channel Matrix multi-channel pipette, 35 µL of the working solution of HDAC4 catalytic domain enzyme (0.286 µg/mL in assay buffer) is transferred to the assay plate. The assay is then started by adding 10 µL of 5× (50 µM) substrate to the assay plates using either the Bravo, Janus or 16-channel Matrix multi-channel pipette. The assay plate is then shaken for two minutes on an orbital shaker at 900 rpm (rotations per minute). Next the plate is incubated for 15 minutes at 37° C. The reaction is stopped by adding 25 µL of 3× (30 µM) developer/stop solution to the assay plates using either the Bravo, Janus or a 16-channel Matrix multi-channel pipette. Assay plates are then shaken for 5 minutes on an orbital shaker at 1200 rpm. Next, the assay plates are incubated at 37° C. for 1 hour in a tissue culture incubator. Finally, the fluorescence is measured (Excitation: 355 nm, Emission: 460 nm) using PerkinElmer EnVision in top read mode.

Example 5: Analysis of Inhibition of HDAC5

The potency of exemplifying compounds described herein is quantified by measuring the Histone Deacetylase 5 (HDAC5) enzymatic activity using the Class IIa selective substrate, Boc-Lys(Tfa)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially Dilute the Compounds.

Serial dilutions of the compounds to be tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either Bravo, Janus, or a 12.5 µL 16-channel Matrix multi-channel pipette. Each well with the 2 µL of the 200× stamped compound solution is diluted 1:20 by the addition of 38 µL assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC5 Catalytic Domain Enzyme (0.57 µg/mL).

The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/mL stock aliquot of HDAC5 catalytic domain (thawed on ice) diluted to 0.57 µg/mL with assay buffer (50 mM Tris-HCl, 137 mM NaCl, 2.7 mM KCl, and 1 mM MgCl$_2$ at pH 8 and equilibrated to 37° C.) just prior to the addition of the enzyme to the assay.

Prepare 5× (40 µM) Boc-Lys(Tfa)-AMC Substrate.

5× (40 µM) substrate is prepared just prior to the addition to the assay. The 5× substrate is prepared by diluting the 100 mM Boc-Lys(Tfa)-AMC in DMSO solution 1:2500 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µL of each solution of the 1:20 diluted compounds and controls from above is transferred to a clear bottomed, black, 384-well assay plate using the Bravo or Janus. Using a 16-channel Matrix multi-channel pipette, 35 µL of the working solution of the HDAC5 catalytic domain enzyme (0.57 µg/mL in assay buffer) is transferred to the assay plate. The assay is then started by adding 10 µL of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µL of 3× (30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example 6: Analysis of Inhibition of HDAC7

The potency of exemplifying compounds described herein is quantified by measuring the Histone Deacetylase 7 (HDAC7) enzymatic activity using the Class IIa selective substrate, Boc-Lys(Tfa)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially Dilute the Compounds.

Serial dilutions of the compounds to be tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 µL (200×) of each diluted solution and each control (full activity: 100% DMSO alone or full inhibition 1 mM) is stamped into V-bottom polypropylene 384-well compound plates using either the Bravo, Janus, or a 12.5 µL 16-channel Matrix multi-channel pipette. Each well with the 200× compound solution is diluted 1:20 by the addition of 38 µL assay buffer+DMSO (10.5% DMSO, 45 mM Tris-HCl, 123 mM NaCl, 2.4 mM KCl, and 0.9 mM MgCl$_2$ at pH 8.0 and equilibrated to 37° C.).

Prepare HDAC7 Enzyme (71 ng/mL).

The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/mL stock aliquot of HDAC7 (thawed on ice) diluted to 71 ng/mL with assay buffer (50 mM Tris-HCl, 137 mM NaCl, 2.7 mM KCl, and 1 mM MgCl$_2$ at pH 8 and equilibrated to 37° C.) just prior to the addition of enzyme to the assay.

Prepare 5× (50 µM) Boc-Lys(Tfa)-AMC Substrate.

5× (50 µM) substrate is prepared just prior to the addition to the assay. The 5× substrate is prepared by diluting a 100 mM Boc-Lys(Tfa)-AMC in DMSO solution 1:2000 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/mL trypsin equilibrated to 37° C.

Assay.

5 µL of each solution of 1:20 diluted compound from above is transferred to a clear bottomed, black, 384-well assay plate using the Bravo or Janus. Using a 16-channel Matrix multi-channel pipette, 35 µL of the working solution of the HDAC7 enzyme (71 ng/mL in assay buffer) is transferred to the assay plate. The assay is then started by adding 10 µL of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µL of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example 7: Analysis of Inhibition of HDAC9

The potency of exemplifying compounds described herein is quantified by measuring the Histone Deacetylase 9 (HDAC9) enzymatic activity using the Class IIa selective substrate, Boc-Lys(Tfa)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially Dilute the Compounds.

Serial dilutions of the compounds to be tested and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µL aliquots of the 10 mM compound in DMSO are prepared and stored at −20° C. From one stock aliquot of each compound to be tested and the reference compound, a 16-point serial dilution is prepared according to Table 1 using a 125 µL 16-channel Matrix multi-channel pipette.

2 μL (200×) of each diluted solution and each control (full activity: 100% DMSO alone or full inhibition 1 mM) is stamped into V-bottom polypropylene 384-well compound plates using either the Bravo, Janus, or 12.5 μL 16-channel Matrix multi-channel pipette. Each well with the stamped 200× compound solution is diluted 1:20 by the addition of 38 μL assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 Enzyme (0.57 μg/mL).

The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/mL stock aliquot of HDAC9 (thawed on ice) diluted to 0.57 μg/mL with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 μM) Boc-Lys(Tfa)-AMC Substrate.

5× (125 μM) substrate is prepared just prior to the addition to the assay. The 5× substrate is prepared by diluting a 100 mM Boc-Lys(Tfa)-AMC in DMSO solution 1:800 by adding it drop-wise to assay buffer (equilibrated to 37° C.) while vortexing at slow speed to prevent precipitation.

Prepare 3× (30 μM) Developer/Stop Solution.

3× (30 μM) Developer/Stop Solution is prepared just prior to addition to the plate by diluting a stock solution of 10 mM reference compound 1:333 in 25 mg/mL trypsin equilibrated to 37° C.

Assay.

5 μL of each solution of 1:20 diluted compound from above is transferred to a clear bottomed, black, 384-well assay plate using the Bravo or Janus. Using a 16-channel Matrix multi-channel pipette, 35 μL of the working solution of the HDAC9 enzyme (0.57 μg/mL in assay buffer) is transferred to the assay plate. The assay is then started by adding 10¢ of 5× (125 μM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 μL of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the EnVision. Finally, the fluorescence is measured (Excitation: 355 nm, Emission: 460 nm) using PerkinElmer EnVision in top read mode.

Example 8: Analysis of Inhibition of Cellular HDAC Activity

The potency of exemplifying compounds described herein is quantified by measuring the cellular histone deacetylase enzymatic activity using the Class IIa selective substrate, Boc-Lys(Tfa)-AMC. After penetration in Jurkat E6-1 cells, the substrate is deacetylated to Boc-Lys-AMC. After cell lysis and cleavage by trypsin, the fluorophore AMC is released from the deacetylated substrate only. The fluoresence of the sample is directly related to the histone deacetylase activity in the sample.

Jurkat E6.1 Cell Culture and Plating.

Jurkat E6.1 cells are cultured according to standard cell culture protocols in Jurkat E6.1 Growth Media (RPMI without phenol red, 10% FBS, 10 mM HEPES, and 1 mM Sodium Pyruvate). Jurkat E6.1 cells are counted using a Coulter Counter and resuspended in Jurkat E6.1 growth media at a concentration of 75,000 cells/35 μL. 35 μL or 75,000 cells is seeded into Greiner microtitre assay plates. The plates are then incubated at 37° C. and 5% $CO_2$ while other assay components are being prepared.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 70 μL aliquots of the 10 mM compound in DMSO are prepared and stored at −20° C. From one stock aliquot of each compound to be tested and the reference compound, a 16-point serial dilution is prepared according to Table 1 using a 125 μL 16-channel Matrix multi-channel pipette.

2 μL (200×) of each diluted solution and each control (full activity: 100% DMSO alone or full inhibition 1 mM) is stamped into V-bottom polypropylene 384-well compound plates using either the Bravo, Janus, or 12.5 μL 16-channel Matrix multi-channel pipette. Each well with the 200× compound solution is diluted 1:20 by the addition of 38 μL Jurkat assay buffer+DMSO (9.5% DMSO, RPMI without phenol red, 0.09% FBS, 9 mM Hepes, and 0.9 mM Sodium Pyruvate equilibrated to r.t.)

Prepare 5× (500 μM) Boc-Lys(Tfa)-AMC Substrate.

5× (500 μM) substrate is prepared just prior to the addition to the assay. The 5× substrate is prepared by diluting a 100 mM Boc-Lys(Tfa)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer.

10 mL of 3× lysis buffer is prepared with 8.8 mL of 3× stock lysis buffer (50 mM Tris-HCl, pH 8.0, 137 mM NaCl, 2.7 mM KCl, 1 mM $MgCl_2$, 1% Nonidet P40 Substitute equilibrated to r.t.) and 1.2 mL of 3 mg/mL Trypsin equilibrated to r.t.

Assay.

5 μL of each solution of 1:20 diluted compound from above is transferred to the Greiner microtitre assay plates with 75,000 cells/well using the Bravo. Cells are then incubated for 2 hours at 37° C. and 5% $CO_2$. The assay is then started by adding 10 μL of 5× (500 μM) substrate to the assay plate using either the Bravo or 16-channel Matrix multi-channel pipette. The cells are then incubated for 3 hours at 37° C. and 5% $CO_2$. Next, 25 μL of 3× lysis buffer is added to each well using either the 125 μL 16 channel pipette or the Bravo. The assay plate is then incubated overnight (15-16 hours) at 37° C. and 5% $CO_2$. The following day, the plates are shaken on an orbital shaker for 1 minute at 900 rpm. Finally the top read fluorescence (Excitation: 355 nm, Emission: 460 nm) is measured using PerkinElmer EnVision.

Example 9. Compound 6 PK Study

Following iv administration at a nominal dose of 5 mg eq./Kg Compound 6 exhibited an apparent bi-phasic elimination. Therefore the clearance value of 6.4 L/h/Kg (>liver plasma flow) for Compound 6, is considered to be an average of the clearance phases (data in Tables 2 and 3).

There were insufficient data to characterise the terminal elimination half-life in plasma for Compound 6. Using half-life values determined in plasma or brain tissue and the volume of distribution at steady state, the clearance of the terminal phase was estimated to be 0.13 L/hr/Kg (<5% liver plasma flow) for Compound 6. Evidence of glucuronidation was observed during sample analysis, therefore direct conjugation of the hydroxamate is a potential clearance mechanism.

Following oral dosing (nominal 10 mg/Kg) Compound 6 was absorbed rapidly ($t_{max}$ 0.25 h post dose) and its bioavailability was determined to be good (32%).

Compound 6 distributed into brain and muscle tissue with average tissue to plasma ratios increasing over the time course of the studies. As evidenced by individual tissue:plasma ratios, Compound 6 showed high tissue distribution. The volume of distribution of Compound 6 was calculated as being 1.1 L/Kg.

Example 10. Compound 8 PK Study

Higher brain penetration and volume of distribution were observed with Compound 8 (data shown in Table 2) compared to other compounds.

Compound 8 Dose Escalation PK Study

Compound 8 was progressed into a dose escalation study (PO administration to C57Bl6 mice, 30 and 100 mg eq./kg). The concentrations of Compound 8 determined in plasma, brain and muscle from this study and the previous study where Compound 8 was administered PO at 10 mg/kg are shown in Tables 2 and 3.

Plasma, brain and muscle concentrations of Compound 8 following PO administration at 10 mg/kg, 30 mg/kg and 100 mg/kg are shown in FIG. 1.

Following oral doses (30 and 100 mg eq./kg), the compound was absorbed rapidly with $C_{max}$ occurring at 0.5 hours post dose. The plasma $AUC_{0-last}$ appeared linear with increasing dose levels with a dose normalised value of approximately 300 nM·hr·kg/mg. However, $C_{max}$ did not show a linear increase suggesting that dissolution may be decreasing the rate of absorption, but not its extent, with increasing dose. Bioavailability was good at ca. 35% for both dose levels.

Evidence of glucuronidation was observed during sample analysis, therefore direct conjugation of the hydroxamate is a potential clearance mechanism for this compound.

Compound 8 showed good distribution into brain and muscle tissue. Terminal half-lives could not be determined accurately but were estimated to be 4.8 h (PO 30 mg/kg) and 3.4 h (PO 100 mg/kg) hours in brain and 5.6 h (PO 30 mg/kg) and 4.1 h (PO 100 mg/kg) in muscle.

When compared to the 30 mg/Kg PO data, dose normalized brain and muscle AUCs decreased by approximately 20% when Compound 8 was dosed at 100 mg/kg suggesting that brain permeability and penetration into the muscle is approaching saturation, similar to that seen for Compound 6. Additionally, $t_{max}$ was shown to be later (1 h) at the higher dose level, further indicating that the rate of absorption of Compound 8 is decreasing with increased dose.

Compound 8: absorption, distribution, metabolism, and excretion profiling, thermodynamic solubility and dose formulation studies Compound 8 was shown to be highly bound to plasma proteins (3% unbound) and brain tissue (0.5% unbound) in contrast to the low plasma protein and brain tissue binding determined for Compound 6 (20% and 10% unbound respectively).

The thermodynamic solubility of Compound 8 was highest at pH 9 but determined to be moderate at all pHs (0.012-0.035 mg/mL).

Example 11. Hepatic Microsomal Stability (Half-Life)

Incubations of test compounds (1 µM initial concentration, n=2) were carried out with pooled hepatic microsomes (0.25 mg protein/mL in 0.1 M phosphate buffer pH7.4). NADPH (1 mM) was added to initiate the reactions. The incubations were performed at 37° C. Samples (100 µL) were taken from the incubation at 0, 5, 10, 20 and 40 min and added to 100 µL of acetonitrile containing carbamazepine as analytical internal standard, to terminate the reaction. Samples were centrifuged and the supernatant fractions analysed by LC-MS/MS. The instrument responses (i.e. chromatographic peak heights), normalized by internal standard response were referenced to the zero time-point samples (as 100%) in order to determine the percentage of compound remaining.

Ln plots of the % remaining, for each compound, were used to determine the half-life for the microsomal incubations.

Half-life values were calculated from the relationship $$T\frac{1}{2}(\text{min}) = -0.693/\lambda$$

where $\lambda$ was the slope of the Ln concentration vs time curve.

The in vitro intrinsic clearance, $CL_{int}$ (µL/min/mg microsomal protein), was calculated using the following formula:

$$Cl_{int} = 0.693 \times 1/T_{1/2}(\text{min}) \times \text{incubation volume (µL)/mg of microsomal protein}$$

The in vitro intrinsic clearance, $Cl_{int}$ (mL/min/kg), was calculated and scaled to hepatic extraction ratios using the following scaling parameters and formulae.

Parameters

|  | Value | | |
| --- | --- | --- | --- |
| Parameter | Human | Mouse | Rat |
| Microsomal protein concentration in incubation (mg/mL) | 0.25 | 0.25 | 0.25 |
| microsomes/g liver (mg) | 52 | 52 | 45 |
| liver weight/kg body weight (g) | 25 | 45 | 40 |
| hepatic plasma flow (mL/min/kg) | 11.7 | 50 | 30 |

Formulae $$Cl_{int}(\text{tissue clearance}) \text{ mL/min/kg} = [0.693/t\frac{1}{2}(\text{min})] \times [1/\text{microsomal protein concentration mg/mL}] \times [\text{mg microsomes/g liver}] \times [\text{g liver/kg body weight}]$$

$$Cl_{int}(\text{hepatic clearance}) \text{ mL/min/kg} = \text{hepatic plasma flow} \times Cl_{int}/(\text{hepatic plasma flow} + Cl_{int})$$

Hepatic extraction ratio $(Eh) = Cl_{int}$(hepatic clearance) mL/min/kg/hepatic plasma flow (mL/min/kg)

Permeability and Effective Efflux Ratio in MDCK-MDR1

The MDR1-MDCKII and wild type MDCKII cell lines were cultured in accordance with the guidelines provided by Solvo Biotechnology. Both wild-type MDCK and MDR1-

MDCK cells were seeded at a cell density of 2.3×10⁵ cells/well into 24-well Transwell plates and cultured for three days to form monolayers. Test compound was loaded into the donor compartments of the Transwell plate (24-well) bearing MDR1-MDCK or wild type MDCK monolayers. Test compound was added to either the apical or basolateral chambers of the Transwell plate assembly at a concentration of 10 µM in Hanks' Balanced Salt Solution containing 25 mM HEPES (pH 7.4). Lucifer Yellow was added to the apical buffer in all wells and its permeation monitored to assess integrity of the cell layer. As Lucifer Yellow (LY) cannot freely permeate lipophilic barriers, a high degree of LY transport indicates poor integrity of the cell layer and wells with LY permeability above 100 nm/s are rejected.

After 1 h incubation at 37° C., aliquots were taken from both chambers and added to acetonitrile containing analytical internal standard (carbamazepine) in a 96-well plate. Concentrations of compound in the samples were measured by LC-MS/MS. Concentrations of LY in the samples were measured using a fluorescence plate reader.

The apparent permeability ($P_{app}$) values of test compound were determined for both the apical to basal (A>B) and basal to apical (B>A) permeation and the efflux ratio (B>A:A>B) determined in both the wild type MDCK and MDR1-MDCK cells.

Apparent permeability ($P_{app}$) values were calculated from the relationship:

$$P_{app}(\text{cm/sec} \times 10^{-6}) = \left[\frac{\text{compound}_{acceptor\ final} \times V_{acceptor} \times V_{donor}}{\text{compound}_{donor\ initial} \times V_{donor} \times T_{inc} \times \text{surface area}}\right] \times 10^6$$

Where V=chamber volume and $T_{inc}$=incubation time in seconds.

Donor=Chamber of Transwell to which compound is dosed: apical for A>B experiments and basal for B>A experiments.

Acceptor=Chamber of Transwell in to which permeation of compound is measured: basal for A>B experiments and apical for B>A experiments.

The Efflux ratios, as an indication of active efflux from the apical cell surface, were calculated using the ratio of $P_{app}$ B>A/$P_{app}$ A>B.

The effective efflux ratio was also determined from the ratio observed in MDR1-MDCK cells relative to the ratio observed in wild-type cells. Known substrates for human MDR1 typically display effective efflux ratios of greater than two.

The data are shown in Tables 2 and 3.

TABLE 2

| | | |
|---|---|---|
| cat. HDAC4 IC$_{50}$ (µM) | 0.049 | 0.044 |
| HDAC4 (bioch) IC$_{50}$ (µM) | 0.04 | 0.06 |
| HDAC4 (cell) IC$_{50}$ (µM) | 0.11 | 0.07 |
| cat. HDAC5 IC$_{50}$ (µM) | 0.023 | 0.060 |
| cat. HDAC7 IC$_{50}$ (µM) | 0.026 | 0.031 |
| cat. HDAC9 IC$_{50}$ (µM) | 0.040 | 0.050 |
| cat. HDAC3 IC$_{50}$ (µM) | 25.1 | 25.8 |
| cat. HDAC8 IC$_{50}$ (µM) | 6.7 | 9.1 |
| cat. HDAC6 IC$_{50}$ (µM) | 3.0 | NT |
| Boc-Lys(Tfa) IC$_{50}$ (µM) | 0.12 | 0.059 |
| Boc-Lys(Ac) IC$_{50}$ (µM) | >50 | >50 |
| M$_w$ | 337 | 391 |
| tPSA [Å$^2$] | 75 | 75 |
| AlogP | 2.3 | 3.4 |
| kinetic solubility (mg eq./mL) | 0.059 | 0.056 |
| effective efflux ratio (MDR1-MDCK/wt-MDCK) | 3.0 | 1.2 |
| MDCK PAPP_A_B (nm/s) | 280 | 294 |
| human liver m/somes Cl$_{int}$ ml/min/Kg BW | <36 | <36 |
| mouse liver m/somes Cl$_{int}$ mL/min/Kg BW | 109 | <76 |
| CYP P450 inhibition (µM) | >50 all isozymes tested | >50 all isozymes tested except 3A4, >35 |
| Plasma protein binding (% unbound) | 20 | 3 |
| Brain tissue binding (% unbound) | 9.9 | 0.4 |
| Plasma Cmax$_{norm}$ (nM) po, | 220 | 280 |
| Plasma AUC$_{norm}$ (nM*h) iv | 460 | 830 |
| Plasma Clearance (L/h/kg) | 6.4 | 3.1 |

TABLE 2-continued

| | | |
|---|---|---|
| | 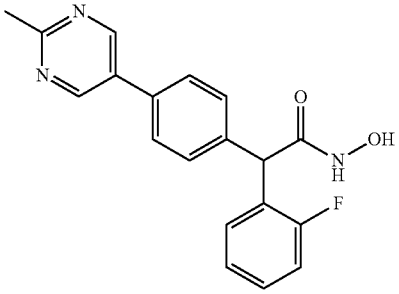 [SMILES: Cc1ncc(-c2ccc(C(C(=O)NO)c3ccccc3F)cc2)cn1] | 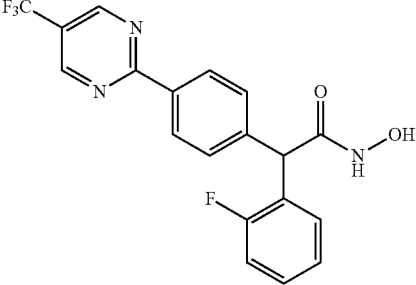 [SMILES: O=C(NO)C(c1ccc(-c2ncc(C(F)(F)F)cn2)cc1)c1ccccc1F] |
| Volume$_{SS}$ (L/kg) | 1.1 | 7.3 |
| iv t$_{1/2}$ (h) | Pl NC | Pl 3.4 |
| | Br 5.7 | Br 2.0 |
| | Mu 8.4 | Mu NC |
| Oral Bioavailability (%) | 32 | 44 |
| Br:Pl ratio iv | 0.2-4.5:1 | 1.5-4.9:1 |
| Mu:Pl ratio iv | 0.9-12:1 | 1.0-2.7:1 |
| Plasma Cmax$_{norm}$ (nM) po | 200, 160 | 132, 70 |
| Plasma AUC$_{norm}$ (nM*h) iv | 930 | — |
| Plasma AUC$_{norm}$ (nM*h) po | 250, 250 | 300, 290 |
| Plasma Clearance (L/h/kg) | 3.2 | — |
| Volume$_{SS}$ (L/kg) | 1.04 | — |
| iv t$_{1/2}$ (h) | Pl 2.2 | — |
| | Br 5.4 | |
| | Mu 7.0 | |
| po t$_{1/2}$ (h) | Pl 1.9, 1.2 | NC |
| | Br 4.4, 3.6 | |
| | Mu 8.2, 8.8 | |
| Oral Bioavailability (%) | 27, 27 | 36, 35 |
| Tissue:Plasma | Br:Pl 0.1-3.7:1, Mu:Pl 0.5-23:1 | Br:Pl 0.2-2.2:1, Mu:Pl 0.4-1.9:1 |

Key:
NT Not tested
NC Not calculated due to insufficient data points
NA Not applicable PK parameters due to route
— Study not performed
Br Brain
Pl Plasma
Mu Muscle
AlogP and tPSA calculated with Pipeline Pilot 8.5, Accelrys Software Inc.

TABLE 3

| | Compound 6 | Compound 8 | Comparison compounds | |
|---|---|---|---|---|
| IC$_{50}$ μM (bioch) | 0.04 | 0.06 | 0.07 | 0.09 |
| IC$_{50}$ μM (cell) | 0.11 | 0.07 | 0.64 | 0.55 |
| AlogP | 2.3 | 3.4 | 2.4 | 2.1 |
| MLM (mL/min/kg BW) | 65, 109 | 76 | 93 | 77 |
| MDCK EER | 3.0 | 1.2 | 3.2 | 4.9 |
| Papp A-B (cm/s × 10$^6$) | 280 | 294 | 234 | 175 |
| IV PK Plasma | | | | |
| AUC$_{norm}$ nM*hr kg/mg | 463 | 830 | 409 | 516 |
| Clearance (CL$_p$) | 6.4 | 3.1 | 7.4 | 6.4 |
| Volume of Distribution at Steady State (Vd$_{ss}$) L/Kg | 1.1 | 7.3 | 3.1 | 2.6 |
| Half-life hour | NC | 3.4 | 1.8 | 1.8 |
| Brain | | | | |
| AUC$_{norm}$ nM*hr kg/mg | 274 | 1600 | 511 | 162 |
| Clearance (CL$_p$) | 294 | 3100 | 666 | 172 |
| Half-life hour | 5.7 | 2.0 | 3.3 | 2.2 |
| Brain-plasma | 0.19-4.5 | 1.5-4.9 | 0.54-8.9 | 0.12-2 |
| Muscle | | | | |
| AUC$_{norm}$ nM*hr kg/mg | 900 | 800 | 1048 | 835 |
| Clearance (CL$_p$) | 6915 | 6000 | 2378 | 1689 |
| Half-life hour | 8.4 | NC | 4.8 | 4.0 |
| Brain-plasma | 0.85-9.7 | 0.98-2.7 | 1.9-21 | 1.1-8.9 |

TABLE 3-continued

| | Compound 6 | Compound 8 | Comparison compounds | |
|---|---|---|---|---|
| Oral PK | | | | |
| Plasma | | | | |
| AUC$_{norm}$ nM hr kg/mg | 149 | 360 | 109 | 179 |
| Bioavailability % | 32 | 43 | 27 | 35 |
| Observed C$_{maxNorm}$ nM kg/mg | 215 | 280 | 95 | 257 |
| Half-life hour | NC | NC | NC | 1.9 |
| Brain | | | | |
| AUC$_{norm}$ nM*hr kg/mg | 52 | 480 | 151 | 58 |
| Clearance (CL$_p$) | 23 | 310 | 63 | 50 |
| Half-life hour | 3.3 | 5.1 | NC | 2.7 |
| Brain-plasma | 0.04-0.7 | 0.35-2.6 | 0.67-3.4 | 0.15-1.4 |
| Muscle | | | | |
| AUC$_{norm}$ nM*hr kg/mg | 192 | 290 | 260 | 306 |
| Clearance (CL$_p$) | 901 | 3000 | 145 | 264 |
| Half-life hour | 5.5 | NC | NC | 4.0 |
| Muscle-plasma | 0.12-4.1 | 0.56-3.1 | 1.5-5.2 | 1.0-8.0 |

NC: Not calculated, insufficient data points
AlogP calculated with Pipeline Pilot 8.5, Accelrys Software Inc.

TABLE 4

Fold Selectivity (bioch)

| | | |
|---|---|---|
| HDAC4 (μM) | 0.06 | 0.09 |
| HDAC5:HDAC4 | 0.9 | 0.3 |
| HDAC7:HDAC4 | 0.5 | 0.8 |
| HDAC9:HDAC4 | 0.8 | 1 |
| HDAC3:HDAC4 | 400 | 320 |
| HDAC8:HDAC4 | 140 | 60 |
| HDAC6:HDAC4 | ND | 50 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A method for treating a condition or disorder mediated by at least one histone deacetylase in a patient in need of such a treatment, wherein the method comprises administering to the patient a compound of Formula I:

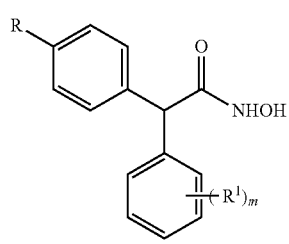

Formula I or a pharmaceutically acceptable salt thereof, wherein
R is pyrimidine substituted with 1 or 2 groups independently chosen from halo, $C_1$-$C_4$ alkyl, and $C_1$-$C_4$ haloalkyl;
each $R^1$ is independently chosen from halo, $C_1$-$C_4$ alkyl, and $C_1$-$C_4$ haloalkyl; and
m is 1, 2 or 3;
and wherein the condition or disorder is inflammation, amyotrophic lateral sclerosis (ALS), Alzheimer's disease, Parkinson's disease, diffuse Lewy body disease, cardiac hypertrophy, breast cancer, lung cancer, rhabdomyosarcoma, glioblastoma multiform, hematologic cancer, multiple myeloma, or a muscle wasting disorder.

2. The method of claim 1, wherein R is

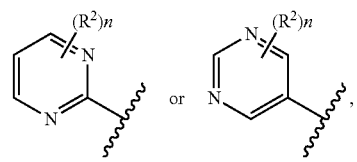

wherein each $R^2$ is independently chosen from halo, $C_1$-$C_4$ alkyl, and $C_1$-$C_4$ haloalkyl;
n is 1 or 2; and
⁓ represents the point of connection to the rest of the molecule.

3. The method of claim 2, wherein n is 1.

4. The method of claim 2, wherein R is

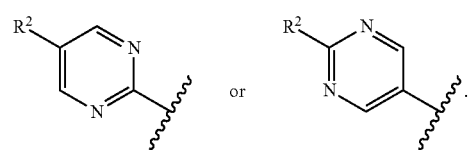

5. The method of claim 2, wherein each $R^2$ is independently $C_1$-$C_4$ alkyl or $C_1$-$C_4$ haloalkyl.

6. The method of claim 5, wherein each $R^2$ is independently methyl or trifluoromethyl.

7. The method of claim 1, wherein R is

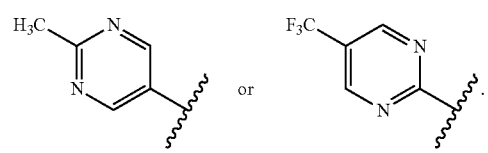

8. The method of claim 1, wherein m is 1.

9. The method of claim 1, wherein at least one $R^1$ is halo.

10. The method of claim 9, wherein at least one $R^1$ is fluoro.

11. The method of claim 10, wherein m is 1, and $R^1$ is 2-fluoro.

12. A method for treating a condition or disorder mediated by at least one histone deacetylase in a patient in need of such a treatment, wherein the method comprises administering to the patient a pharmaceutical composition comprising:

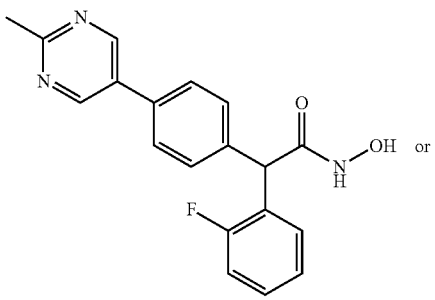

or

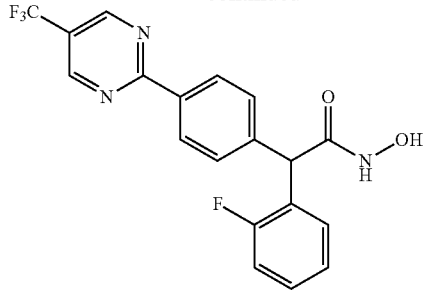 [SMILES: O=C(NO)C(c1ccc(-c2ncc(C(F)(F)F)cn2)cc1)c1ccccc1F]

or a pharmaceutically acceptable salt thereof, and a pharmaceutically acceptable carrier;

and wherein the condition or disorder is inflammation, amyotrophic lateral sclerosis (ALS), Alzheimer's disease, Parkinson's disease, Huntington's disease, diffuse Lewy body disease, cardiac hypertrophy, breast cancer, lung cancer, rhabdomyosarcoma, glioblastoma multiform, hematologic cancer, multiple myeloma, or a muscle wasting disorder.

13. The method of claim 12, wherein the composition is formulated in a form chosen from a tablet, a capsule, a powder, a liquid, a suspension, a suppository, and an aersol.

14. The method of claim 12, wherein the condition or disorder is Huntington's disease.

* * * * *